United States Patent [19]

Harshaw et al.

[11] Patent Number: 5,267,147
[45] Date of Patent: Nov. 30, 1993

[54] PORTABLE CHECKLIST SYSTEM

[75] Inventors: Robert C. Harshaw; Ronald S. Burkey, both of Dallas, Tex.

[73] Assignee: Heads Up Technologies, Inc., Carrollton, Tex.

[21] Appl. No.: 600,529

[22] Filed: Oct. 19, 1990

[51] Int. Cl.$^5$ .................... G06F 15/22; G06F 15/00
[52] U.S. Cl. .................... 364/401; 364/424.06; 364/948.1
[58] Field of Search .................... 364/900, 424.06, 401, 364/405; 340/706, 798; 116/319; 395/600, 650, 700

[56] References Cited

U.S. PATENT DOCUMENTS

| | | | |
|---|---|---|---|
| 4,520,749 | 6/1985 | Jefferson | 116/325 |
| 4,635,030 | 1/1987 | Rauch | 340/52 F |
| 4,654,793 | 3/1987 | Elrod | 364/401 |
| 4,970,683 | 11/1990 | Harshaw et al. | 364/900 |
| 5,068,787 | 11/1991 | Pipella et al. | 364/406 |
| 5,088,037 | 2/1992 | Battaglia | 434/265 |

OTHER PUBLICATIONS

Data Communications, "Better Care, Shorter Stays, Thanks to Networking", Principi et al., Nov. 1986, Copyright 1986 by McGraw-Hill, Inc.

*Primary Examiner*—Robert A. Weinhardt
*Assistant Examiner*—Franktzy Poinvil
*Attorney, Agent, or Firm*—David H. Judson

[57] ABSTRACT

A computerized checklist system for use in the medical field preferably comprises a checklist unit adapted to be held in an operator's hand and a cradle for supporting the checklist unit. Each of these components includes a microprocessor for controlling the operation thereof. An optical link is provided to transmit data between the devices. The checklist unit includes suitable memory for storing alphanumeric checklist data including a sequence of checklist items. A display and a voice synthesizer selectively output checklist items. The checklist unit includes a keypad having a plurality of control switches for enabling an operator of the checklist unit to enter one of a plurality of signals indicating that the operator has taken one of a plurality of predetermined actions in response to each checklist item outputted by on the display and/or spoken by the voice synthesizer. The handheld unit also includes a program, responsive to processing of the checklist items during a work session, for storing a session log, the session log including data identifying each checklist item outputted during the work session, the signal entered by the operator in response to each checklist item, and a time when such signal was entered by the operator. Following placement of the handheld unit in the cradle after the work session, the session log data is downloaded to the cradle and then printed in a predetermined format.

14 Claims, 8 Drawing Sheets

Perfusion Checklist
Session Log Date: 06/05/90 19:33 } 150
Page Printed: 06/05/90 19:34

160 162

N/A APP          164          166   168

|  |  |  |  |  |
|---|---|---|---|---|
|  |  | EMERGENCY CARDIOPULMONARY BYPASS –PROCEDURE | 19:33:40 | GO |
|  |  | EMERGENCY –CHECKLIST | 19:33:40 | GO |
| o | x | Pump –E/O inspection | 19:33:41 |  |
| o | x | Heparin –Given | 19:33:41 |  |
| o | x | Cardiotomy and Oxygenator Gas Vents –Open | 19:33:41 |  |
| o | x | Gas Path Patent, Gas Flow On –Check | 19:33:42 |  |
| o | x | Arterial Line Loaded/Occlusion Set –Check | 19:33:42 |  |
| o | x | Arterial System –Debubbled | 19:33:42 |  |
| o | x | Safety Devices –On | 19:33:43 |  |
| o | x | ACT –Drawn | 19:33:43 |  |
| o | x | Arterial and Venous Lines –Clamped | 19:33:44 |  |
| o | x | Purge Line –Off | 19:33:44 |  |
| o | x | Pump Heads –Covered | 19:33:44 |  |
|  |  | COMPLETE: EMERGENCY –CHECKLIST | 19:33:45 | GO |
|  |  | EMERGENCY CARDIOPULMONARY BYPASS –COMPLETE | 19:33:47 | IO |

N/A catagories: 0
N/A line items: 0

ID Code: 0575 } 158

I have reviewed the foregoing and found it acurate and
true, to the best of my knowledge.
                              154

__________________________________
Primary Perfusionist         } 152

__________________________________
Secondary Perfusionist
           156
Date: ______

Comments:

PORTABLE CHECKLIST SYSTEM

TECHNICAL FIELD

The present invention relates generally to self-contained data storage and display devices and, in particular, to a computerized checklist system that displays and speaks preprogrammed alphanumeric data in a predetermined sequence.

BACKGROUND OF THE INVENTION

Printed checklists have been used extensively in many fields to ensure the safe and consistent operation of sophisticated equipment and systems. For example, during an operation or other medical procedure, a medical specialist must often follow certain instructions in a predetermined manner to enhance the efficacy of a given procedure. Moreover, during the procedure it is often necessary to produce a contemporaneous or "real-time" record associated therewith to verify the operator's diligence during the procedure. Such records can be of critical evidentiary significance should a question arise concerning the proper performance of the procedure.

Misuse of a checklist can have far-reaching consequences. In the medical application, such misuse can create tremendous risks to the patient undergoing the procedure and, of course, increase the attendant liability of the physician. Thus, there is a great need for a checklist management system which is portable and easy to use, which allows the operator to focus on the procedures being implemented rather than on the checklist, which prevents the accidental omission of checklist items, and which enables the operator to produce a contemporaneous record verifying compliance with the checklist.

SUMMARY OF THE INVENTION

It is an object of the invention to provide a novel computerized checklist system for use in the medical field and in other applications in which it is necessary for an operator to have a portable unit for use in sequencing through checklists.

It is still another object of the invention to provide a handheld computer-controlled checklist system which is easy to use and allows the operator to focus his or her attention on procedures instead of recordkeeping tasks.

It is yet another object of the invention to provide a checklist management/recordkeeping device for verifying an operator's compliance with checklist obligations.

It is a further object of the invention to provide a handheld computerized checklist management system that displays and speaks preprogrammed alphanumeric data in a predetermined sequence and then records responses thereto to create a self-authenticating record of an operator's successful compliance with a diagnostic procedure.

These and other objects of the invention are provided in a computerized checklist system comprising a digital processor, storage means connected to the digital processor for storing alphanumeric checklist data including a sequence of checklist items, output means connected to the digital processor for selectively outputting checklist items, program control means for controlling the digital processor to effect presentation, by the output means, of the checklist items, and a plurality of switches for enabling an operator of the checklist system to enter one of a plurality of signals indicating that the operator has taken one of a plurality of predetermined actions in response to each checklist item outputted by the output means. According to the invention, the system further includes program control means, responsive to processing of the checklist items during a work session, for generating a session log. The session log includes data identifying each checklist item outputted during the work session, the signal entered by the operator in response to each checklist item, and a time indication of when such signal was entered by the operator. Moreover, for recordkeeping purposes the system derives a verification code from the session log data. The verification code is uniquely associated with the session log data for the work session. The system also includes printer means for generating a printout of the session log in a predetermined format along with the verification code to facilitate subsequent verification of the session log data.

According to the more specific aspects of the invention, the computerized checklist system comprises two basic components: a checklist unit adapted to be held in an operator's hand, and a cradle for supporting the checklist unit. Each of these components includes a microprocessor for controlling the operation thereof. An optical link is provided to transmit data between the devices. The checklist unit includes suitable memory for storing alphanumeric checklist data including a sequence of checklist items. A display and voice synthesizer selectively output checklist items. The checklist unit includes a keypad having a plurality of control switches for enabling an operator of the checklist unit to enter one of a plurality of signals indicating that the operator has taken one of a plurality of predetermined actions in response to each checklist item outputted by on the display and/or spoken by the voice synthesizer. The handheld unit also includes a program, responsive to processing of the checklist items during a work session, for generating a session log, the session log including data identifying each checklist item outputted during the work session, the signal entered by the operator in response to each checklist item, and a time when such signal was entered by the operator. Following placement of the handheld unit in the cradle after the work session, the session log data is downloaded to the cradle and then printed in a predetermined format.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and for further advantages thereof, reference is now made to the following Description of the Preferred Embodiment taken in conjunction with the accompanying Drawings, in which.

DESCRIPTION OF THE PREFERRED EMBODIMENTS

Figure 1:
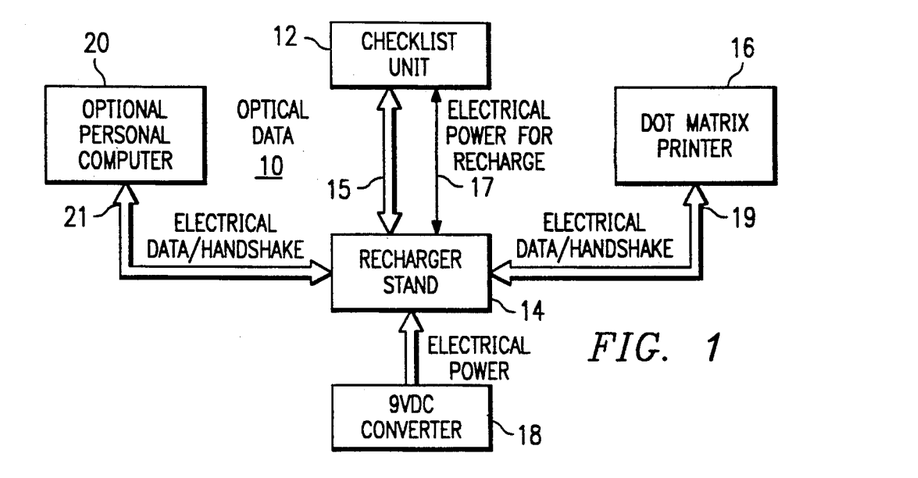
FIG. 1 is a schematic diagram showing the basic components of the portable computerized checklist system of the present invention.

Referring now to FIG. 1, the computerized checklist system of the present invention is generally identified by reference numeral 10. Computerized checklist system 10 includes two (2) primary components: a handheld checklist unit 12 and a charger stand unit 14. The units are connected via an optical link 15 and an electrical power connection 17. The handheld unit 12 is preferably battery-powered and functions to read and manage the checklist for the operator. The charger stand unit 14 provides the necessary mechanical and electrical interfaces for recharging the batteries of the handheld unit 12, as well as the necessary electronics to interface the unit charger 14 to a dot matrix printer 16 via a Centronics parallel data link 19. A voltage converter 18 transforms 110 a.c. line voltage into appropriate d.c. voltages and supplies the electrical power required to recharge the batteries of the handheld unit 12 and drive the charger unit electronics. A personal computer 20 is optionally used and interfaces with the charger unit 14 through a Centronics parallel data link 21.

Figure 2:
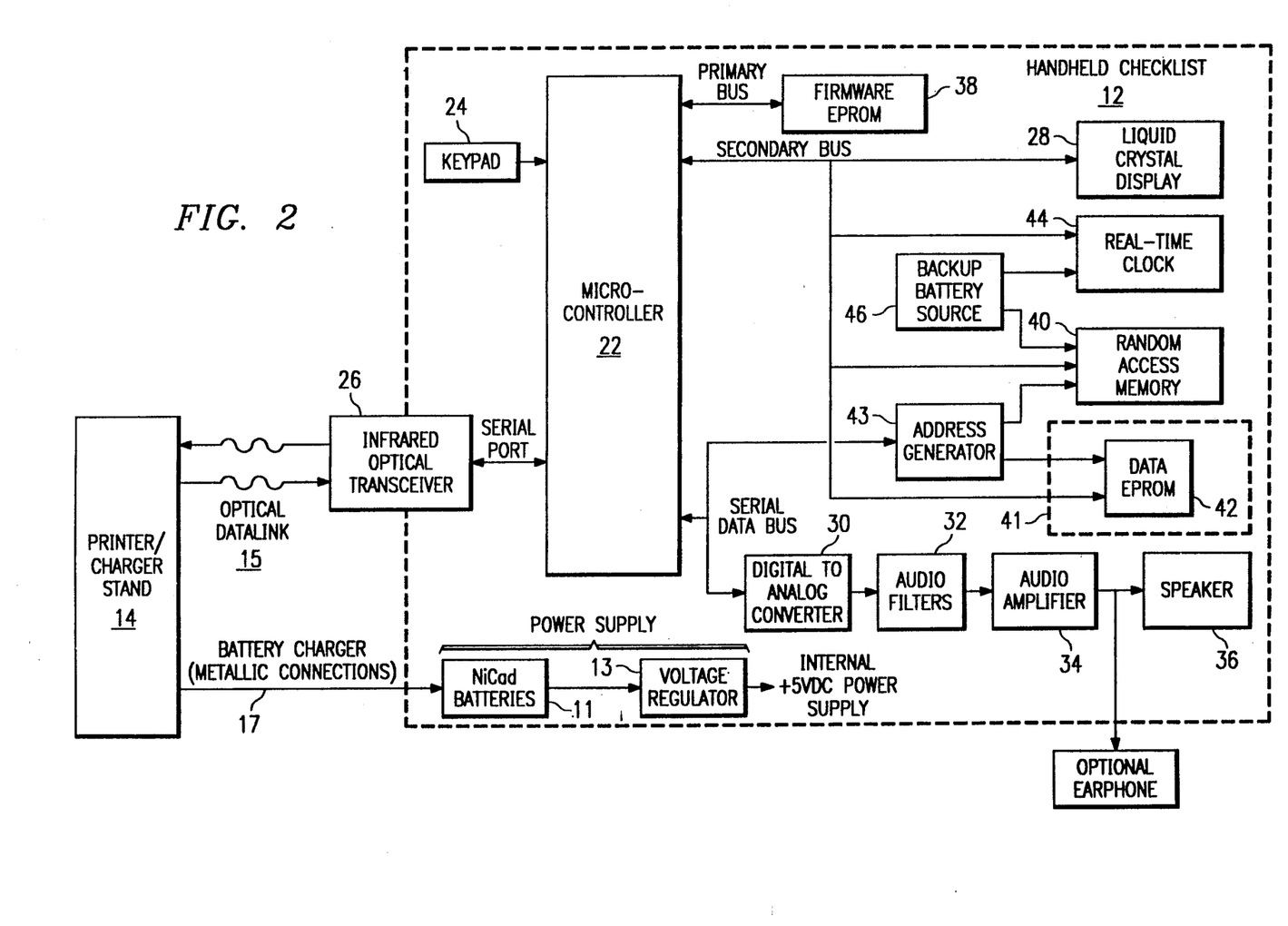
FIG. 2 is a detailed schematic diagram of the handheld checklist unit of the system of FIG. 1.

Referring now to FIG. 2, a detailed schematic diagram is shown of the handheld checklist unit 12. This unit includes a power supply comprising batteries 11 and voltage regulator 13. A microprocessor 22 controls the operation of the device. Microprocessor 22 receives inputs from keypad 24 and infrared optical transceiver 26, and it generates outputs to a liquid crystal display 28 and a voice module or synthesizer comprising digital-to-analog converter 30, audio filter 32, audio amplifier 34 and a speaker 36. Control programs for the microprocessor 22 are supported in firmware EPROM 38, and the unit includes a random access memory (RAM) 40 for use by the microprocessor during processing for storing session log data as will be described. A data EPROM 42 is provided for supporting the checklist in the form of speech data, text data for the display, help screen data, etc. Data EPROM 42 can be supported in a removable cartridge 41 so that (by exchanging cartridges) the device is programmable for different checklists or an alternative checklist application. RAM 40 and EPROM 42 are addressable through the address generator 43 controlled by the microprocessor 22. A real-time clock circuit 44 is also provided to generate real-time indications representing start and stop times of various checklist action items. The RAM 40 and clock circuit 44 are connected to a battery backup source 46 to maintain power thereto should the batteries run down.

The infrared optical transceiver 26 of the handheld checklist unit 10 comprises an infrared light emitting diode (LED) and a phototransistor. The transceiver cooperates with a similar device in the charger unit 14 to create the optical link 15 between the units. In particular, and with reference now to FIG. 3, the charger stand includes a power supply comprising a voltage regulator 52 and a constant current source 54. The output of the voltage regulator drives the internal electronics of the charger while the output of the constant current source is connected by metal connection 17 to the handheld checklist unit 12. The charger unit 14 includes a microprocessor 56 which receives inputs from the infrared optical transceiver 58 and generates outputs to interface circuit 60. Interface circuit 60 is connected to the dot matrix printer 64, while interface circuit 62 is connected to the optional personal computer 64. A firmware EPROM 66 includes the control programs necessary to control the microprocessor 56.

Figure 3:
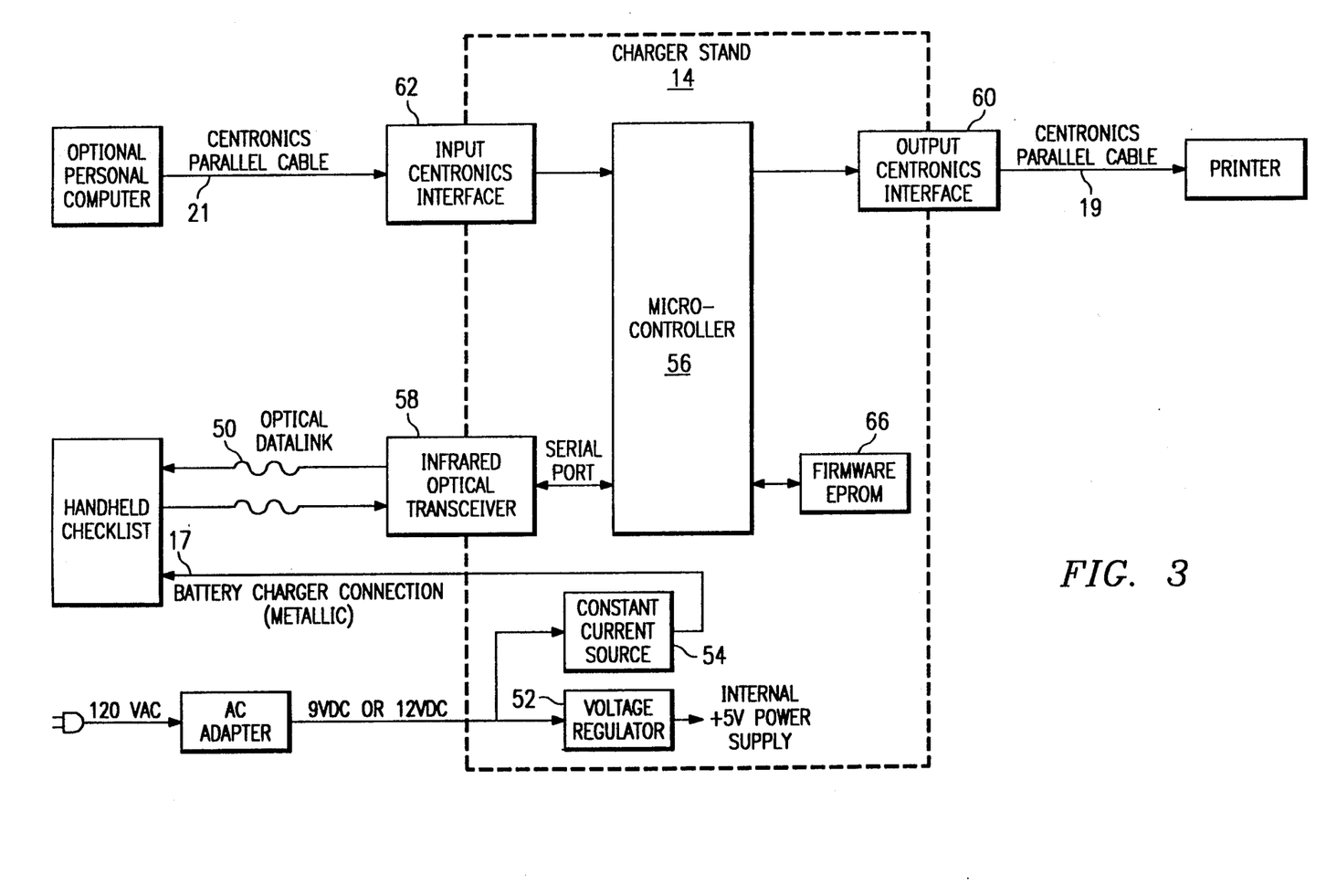
FIG. 3 is a detailed schematic diagram of the charger stand unit of the system of FIG. 1.

The optical link 50 between the checklist unit 12 and the charger unit 14 comprises an uplink (through the LED of the transceiver 58 to the phototransistor of the transceiver 26) and a downlink (through the LED of the transceiver 26 to the phototransistor of the transceiver 58). The link 50 is especially advantageous in the operating room environment where it is required to minimize exposure of the system electronics to fluids and other materials that might otherwise affect the operation of the devices.

Figure 4:
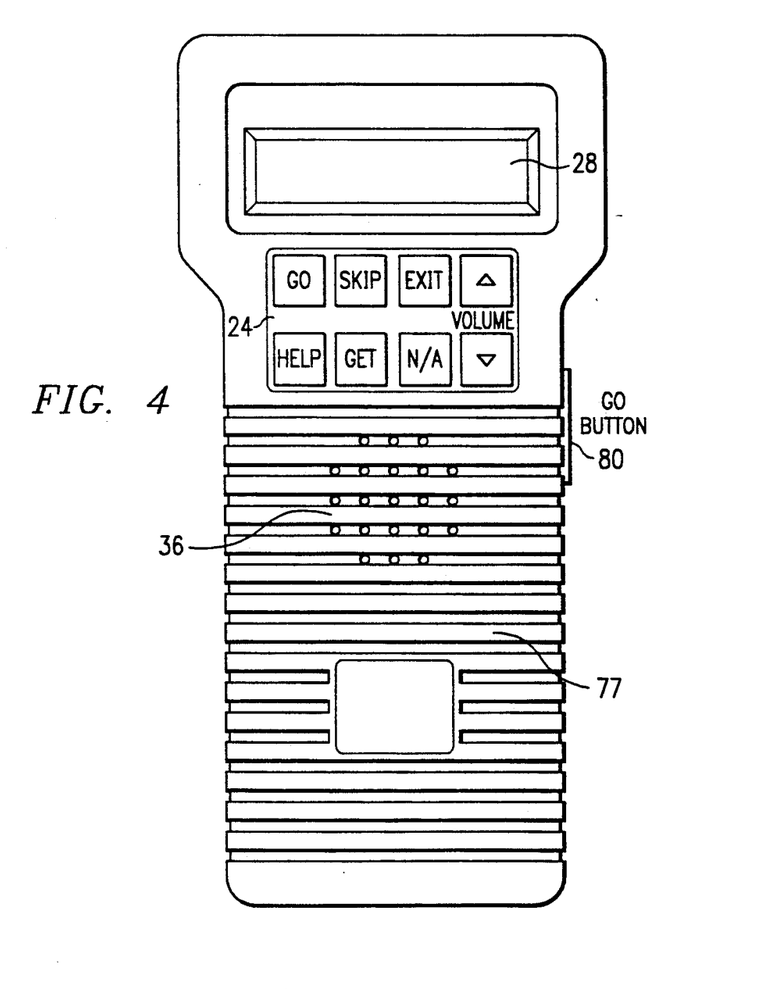
FIG. 4 is a view of the facing portion of the handheld unit of the computerized checklist system of the present invention showing the various switches used to sequence through the checklist.
Figure 5A:
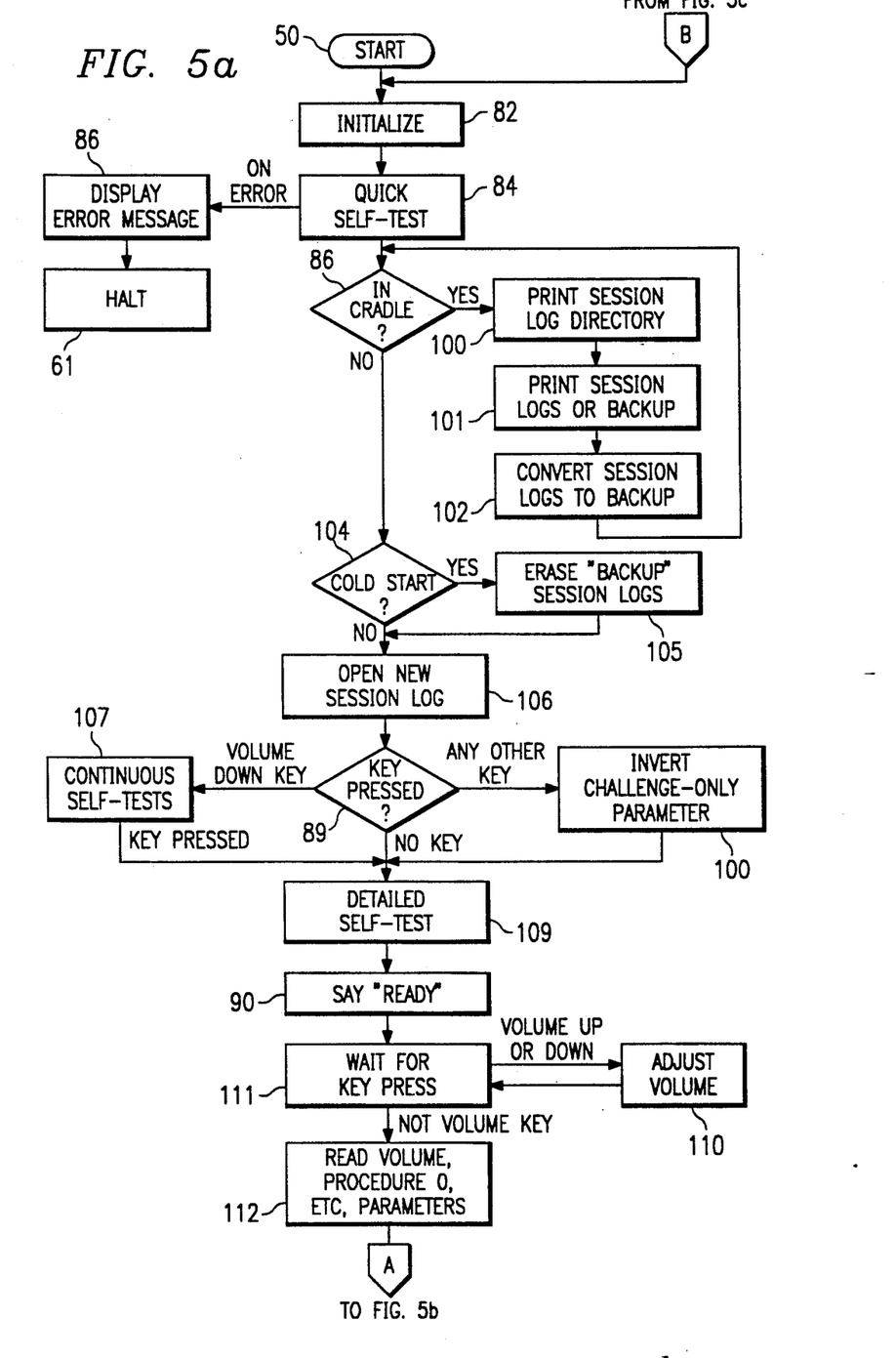
FIGS. 5A-5D are a logic flow diagram illustrating the operation of the present invention.
Figure 5B:
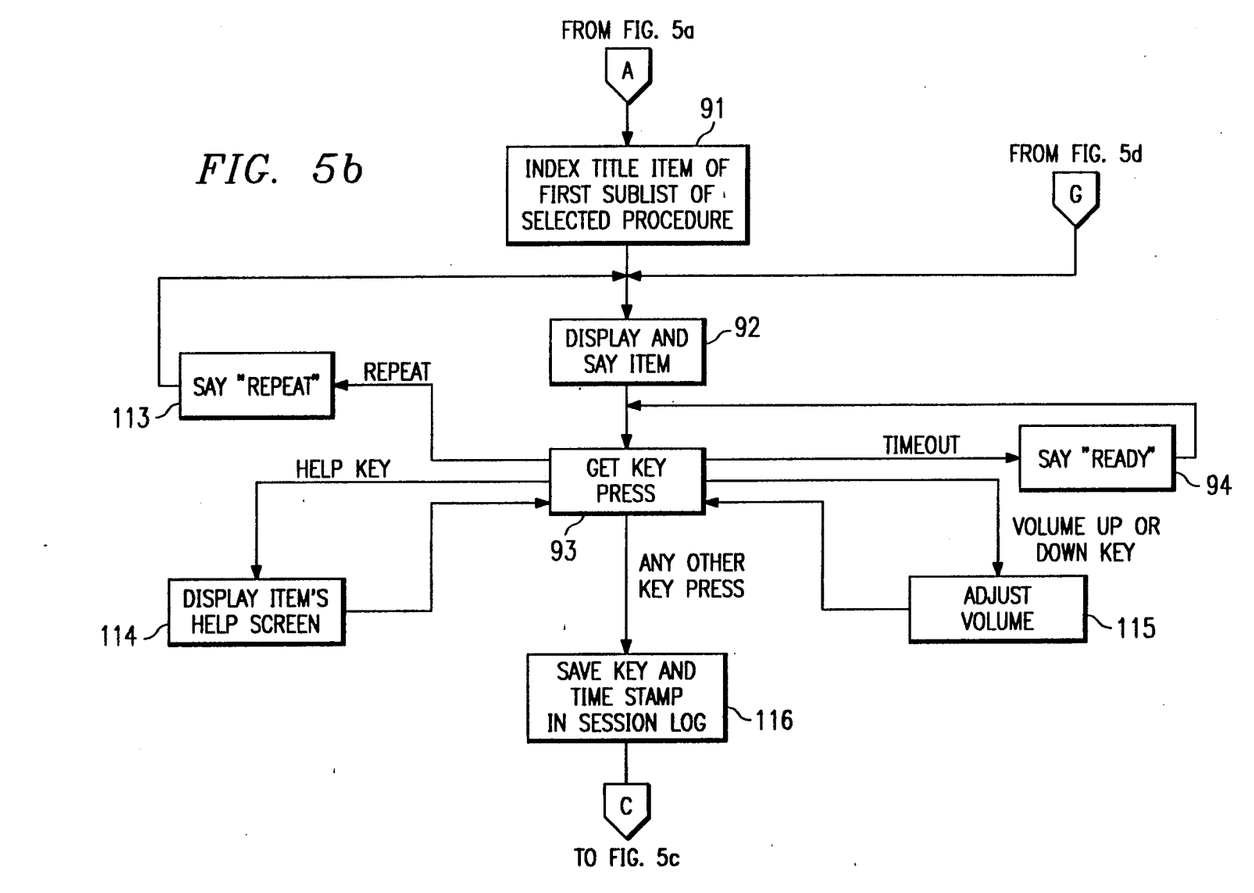
Figure 5C:
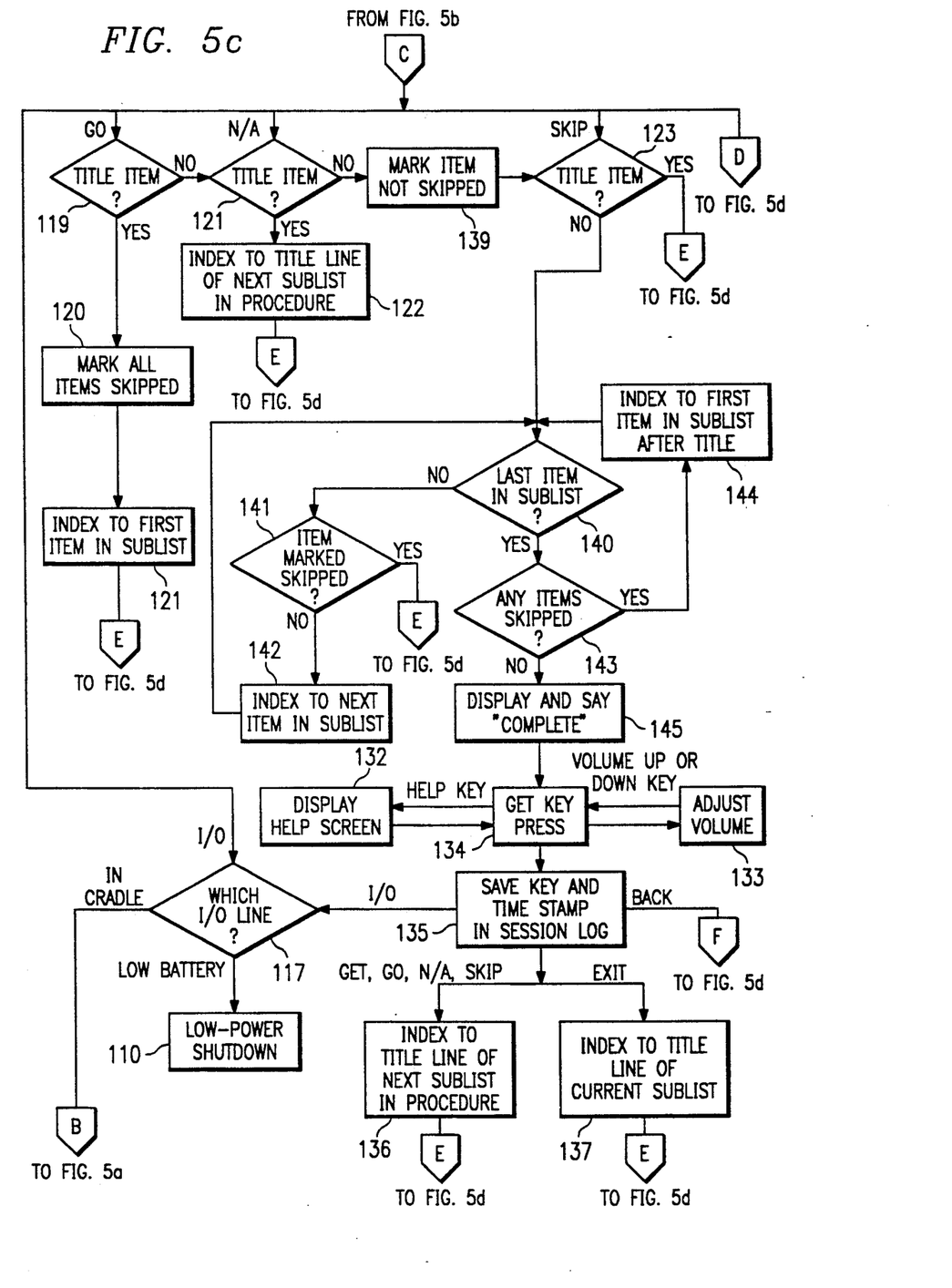
Figure 5D:
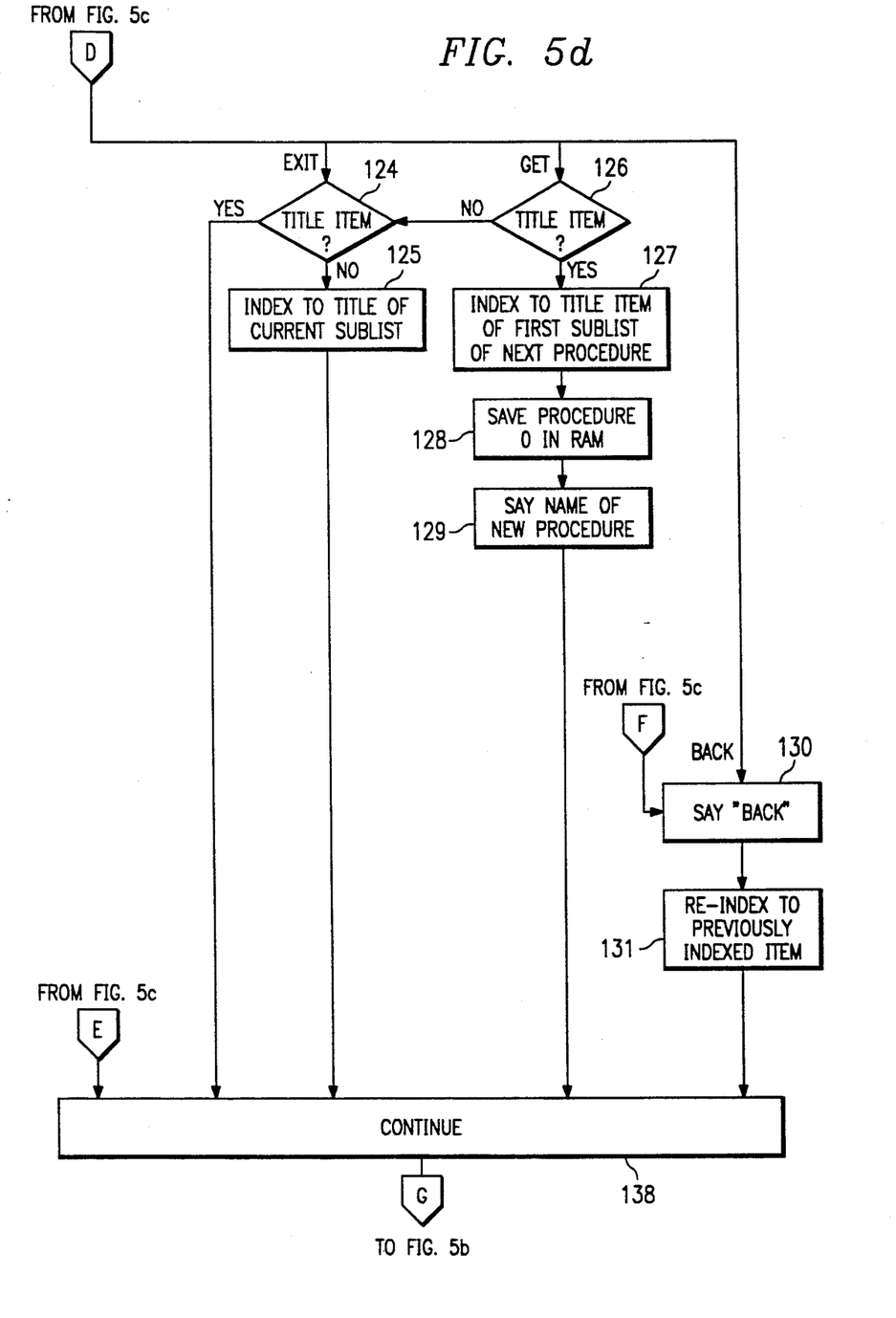

Referring now to FIG. 4, a view of shown of a facing portion 77 of the handheld unit 12. As described above, the unit includes the keypad 24, display 28 and the speaker 36. The keypad includes a plurality of switches for entering commands to control the management of the checklist. According to the invention, a checklist of alphanumeric data is preferably organized into a predetermined sequence of sublists, wherein each of the sublists has a title and includes a predetermined sequence of checklist items. Each checklist item normally includes a "challenge" having a corresponding "response." Typically, but not always, it will be desired to effect presentation of the alphanumeric data in the predetermined sequence of sublists starting with a first sublist and a first checklist item in the first sublist. The switches of the keypad provide control of such presentation and preferably include the following buttons:

1) GO: for entering a checklist category and marking checklist items as completed and thus automatically advance to the next checklist item;

2) SKIP: for marking a checklist item as "not completed" and thus placing the item at the end of a sublist being processed while advancing to the next checklist item in the sublist. Depression of the SKIP button also skips past a sublist;

3) EXIT: for causing all completed items to be marked as not completed and automatically advancing the program to speak and display the title of a current sublist being processed;

4) N/A: for marking the current checklist item as not applicable to the diagnostic routine and advancing to the next item. Items marked N/A are not repeated for action at the end of the sublist;

5) GET: for causing the unit to read another independent checklist which is entered by depressing GO. It operates only when a title line is displayed; and 6) HELP: for causing information about a current item or function to be displayed in a continuous format across the display.

The keypad includes up and down arrow keys for volume control. Although not shown, the keypad may include a BACK key to enable the reprocessing of an item. A REPEAT key may also be used to replay an item if the item was not understood. Depression of the REPEAT key does not affect the "complete" status of the checklist item in any way Alternatively, the "Repeat" and "Back" functions are effected by holding down one of the other buttons (such as the "GO" button) for predetermined times, e.g., one second for "Repeat" and two seconds for "Back." Moreover, the handheld unit also includes a second GO switch 80 mounted in the sidewall of the handheld unit so that the unit can be securely held in the operator's hand while allowing easy access to the GO operation. This feature is especially advantageous in the operating room environment in which the specialist needs to have a free hand for performing tasks associated with the procedure.

In general, the operation of the system 10 is as follows. The operator powers up the hand held computer unit 12, selects the appropriate procedure corresponding to the present situation, and then performs the checklist using the function keys described above. A time-stamped log of each keypress is saved in battery-backed RAM 40 so that a "session log" record is maintained of the performance of that procedure. After the procedure is completed, the operator returns the handheld unit 12 to the recharger stand 14 where the batteries 11 are recharged. If the unit 12 is returned to the stand while it is still powered up, the unit 12 automatically prints a directory of all sessions that have yet to be printed, and also those that have been printed once before. All sessions that have never been printed are automatically printed, and moved to a list of those that have been already printed once. Additionally copies of those logs already printed may be obtained by further interactions with the handheld unit.

Referring now to FIG. 5, a logic diagram is shown of the detailed operation of the portable checklist system of the present invention. The operation begins at step 82 with system initialization. At step 84, the system conducts a self-test. If the system fails the test, the display 24 displays an error message at step 86 and the system halts operations at step 61. If the self-test is passed, a test is performed at step 88 to determine if the handheld unit 12 is in the cradle of the charger unit 14. If not, the unit 40 is supported in the operator's hand and the operation begins.

A test is then performed at step 104 to determine if the procedure is a "cold start," which means that the unit 12 has not been used since a prior session was downloaded and printed. If the result of the test at step 104 is positive, backup session logs are erased at step 105. If the result of the test at step 104 is negative, or following the erasure of the backup logs at step 105, the method continues at step 106 to create a new session log. This log is supported in the RAM 40 of the handheld unit 12 as described above.

At step 89, a test is performed to determine if one of the buttons of the keypad 24 is depressed. If the down arrow key is depressed, continuous self-tests are repeatedly executed at step 107. If any other key is depressed, the method inverts challenge-only parameters at step 108. This enables the unit to speak either "challenge-only," or both "challenge" and "response" depending upon whether the status flag is "1" or "0." In the "challenge-only" mode, "responses" are not announced by the unit. When the operator presses a key to terminate step 107, when step 108 is completed, or if no key is depressed at step 89, the method continues to perform a final self-test at step 109. If the test is passed, the system displays and announces "Ready" at step 90.

The system then enters a waiting mode at step 111 until a key, other than a volume key, is depressed. If a volume key is depressed, the gain of the audio amplifier 34 is adjusted accordingly at step 110. At step 112, the microprocessor 22 reads the volume setting, the first checklist procedure and the procedure parameters. At step 91, the routine indexes to the title of the first sublist of the selected procedure. At step 92, the system displays and announces the next item. After an item has been displayed and announced, the operator must respond by depressing at step 93 one of the buttons of the keypad (or the side-mounted GO button). If a timeout occurs before the operator responds, the system announces "Ready" at step 94 and returns to step 93 awaiting a response. If the HELP key is depressed, the routine displays the item's help screen at step 114 and returns to step 93. If one of the volume arrow keys is depressed, the gain of the audio amplifier 34 is adjusted at step 115 and the routine returns to step 93. If an optional REPEAT key of the keypad is depressed, the system announces "Repeat" at step 113 and returns to step 92 to display and announce the item again. As described above, "Repeat" can be generated by holding down the "GO" button for a predetermined time, e.g., one (1) second.

If any other key is depressed, the routine continues at step 116 to store in the RAM 40 the identity of the key and a time-stamp indication generated by the real-time clock circuit 44. The routine then branches to perform a plurality of checklist management functions depending on which of the keypad buttons is depressed. If the GO button is depressed, a test 119 is performed to determine if the item is a title. If so, the routine marks all items as "skipped" at step 120 and indexes to the first item in the sublist at step 121. The routine then continues at step 138 and returns to step 92 to display and announce the first item in the sublist. If the outcome of the test at step 119 is negative, or if the N/A button is depressed by the operator following step 116, the system performs a test at step 121 to determine if the item is a title. If so, the routine indexes to the title line of the next sublist in the procedure at step 122, continues at step 138 and then returns to step 92 to display and announce the title.

If the result of the test at step 121 is negative, the routine marks the item as not skipped at step 139. If the SKIP button is depressed following step 116, and following step 139, the method performs a test at step 123 to determine if the item is a title. If so, the method continues at step 138 and then returns to step 92 to display and announce the title of the sublist. If the item is not a title of a sublist, the method continues at step 140 to test whether the item is the last item in a sublist. If not, the routine performs a test at step 141 to determine if the item has been marked as skipped. If the item has been marked as skipped as determined by the test at step 141, the routine continues at step 138 and returns at step 92 to display and announce the item. If the item has not been marked as skipped, the routine indexes to the next item in the sublist at step 142 and returns to step 140 to again test whether the item is the last item in the sublist. If the outcome of the test at step 140 is positive, the routine performs a test at step 143 to determine if any items of the sublist were skipped. If so, the routine indexes to the first item in the sublist after the title at step 144 and returns to step 140. If the outcome of the test at step 143 indicates that no items were skipped, the routine advances to step 145 and displays and announces "Complete."

Thereafter, the system waits for a key to be depressed at step 134. Help screens are displayed at step 132 if necessary and/or the volume is adjusted at step 133. The routine continues at step 135 to save the key originally depressed and to generate a time stamp indication in the session log being generated in the RAM 40. If a GET, GO, N/A or SKIP button is then depressed, the routine indexes at step 136 to the title line of the next sublist of the procedure, continues at step 138 and then returns to step 92. If the EXIT button is depressed following step 135, the routine indexes at step 137 to the title line of the current sublist, continues at step 138 and then returns to step 92.

Depression of the EXIT button following step 116 also causes the system to perform a test at step 124 to determine if the item is a title. If so, the routine continues at step 138 and returns to step 92. If the item is not a title, the routine indexes to the title of the current sublist at step 125 and continues at step 138. Finally, if the GET button is depressed, a test is performed at step 126 to determine if the item is a title. If not, the routine defaults to step 124 and continues. If the outcome of the test at step 126 is positive, the routine indexes at step 127 to the title item of the first sublist of the next procedure, saves the new procedure in the RAM at step 128, announces the name of the new procedure at step 129, and then continues at step 138.

As also shown in FIG. 5, the routine is responsive to depression of a BACK key following steps 116 or 135 and announces "Back." As noted above, the "Back" function can alternatively be implemented by depressing the "GO" button for a predetermined time, e.g., two (2) seconds. Thereafter, the routine re-indexes at step 131 to the previously indexed item and continues at step 138. The routine is also responsive to an input/output interrupt following steps 116 or 135 to perform a test at step 117 to determine the nature of the interrupt. If the test indicates a low power situation, a low power shutdown is performed at step 118, although the session log data is retained in the battery-powered RAM 40. If the test at step 117 indicates that the handheld unit 12 has been placed back into the cradle unit 14, the routine returns to step 82. At this point the result of the test at step 88 will be positive and the routine continues, enters a printing mode of operation.

In particular, and according to one important feature of the invention, the session log is then downloaded, through the downlink of the optical link 50, from the RAM 40 of the handheld unit 12, through the charger unit 14 and then to the printer. As described above, the microprocessor 56 of the charger unit controls the printer via the link 19. At step 100, a session log directory of all sessions that have yet to be printed (or have been printed before) is printed. At step 101, the routine continues to print the current session log data. At step 102, logs are converted from "unprinted" to "backup" status.

Figure 6:
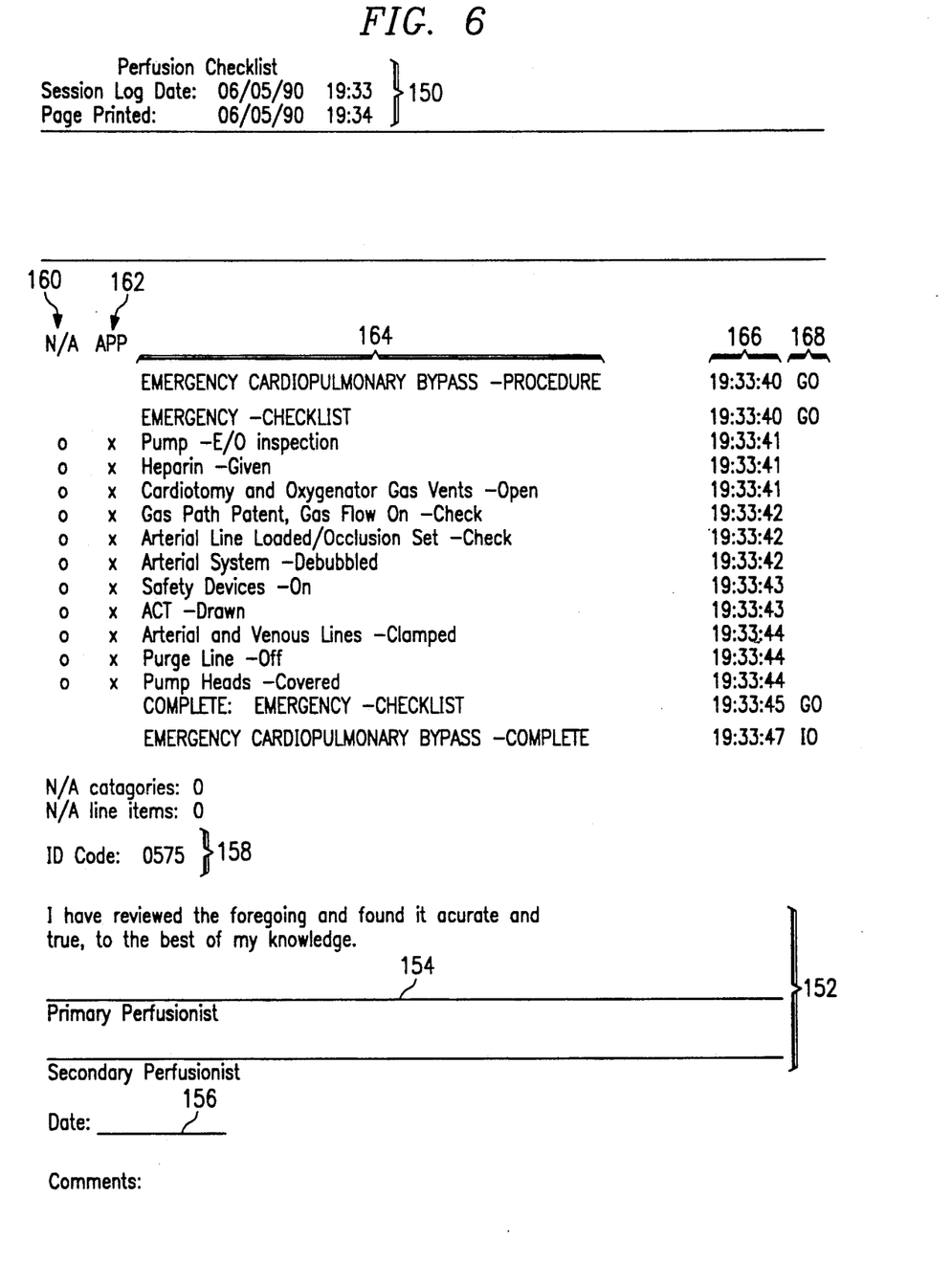
FIG. 6 is a representative session log which is generated according to the teachings of the invention to enable subsequent verification of checklist procedures.

Referring now to FIG. 6, an example is shown of a representative session log. As can be seen, the log includes various session log directory information in an identifier field 150. The log includes several column fields: an N/A field 160, an APP (or "applicable") field 162, a checklist item field 164, a time field 166 and a response field 168. The title of the procedure is printed above the checklist item field 164 as well as a time stamp indicating when the procedure was entered (by depression of the GO button as indicated). The various checklist items are then displayed in sequential order as well as the various times at which the items were displayed and announced. If "GO" were depressed, an "x" is placed in the APP field 162; an "x" is placed in N/A field 160 if "N/A" were depressed. For procedure or sublist titles, these indications (or any other buttons) appear in field 168 instead. The session log also indicates when the sublist was COMPLETE, as well as the time at which the handheld unit was placed back into the cradle (as indicated by the IO in the last column). The session log further includes a verification field 152 which includes one or more attestation lines 154 and a date line 156.

According to another feature of the invention, before the session log data is downloaded to the charger unit for printing, a control routine controls the microprocessor 22 to generate a security or ID Code which is also printed in an ID code field 158 of the session log. The ID Code is preferably generated by calculating a checksum of all bytes printed on a page, post-encrypted by a mathematical formula. In particular, after the checksum is calculated (based on the number of and type of actual data characters printed on the session log page) this value (which is a two-byte number) is exclusive-or'd (bit-by-bit) with a (secret) two-byte bit mask to create the ID Code. Once the ID Code for the page (and thus the session log is originally calculated), any change to the session log printout data will necessarily produce a different ID Code. In other words, the session log data will map into a unique security code and no other security code. This feature of the invention creates a self-authenticating record of the session which cannot be altered without being immediately recognized.

The computerized checklist system of the present invention is designed to function like an additional member of the medical team whose only responsibility is to read, manage and document the checklist. The operator does not have to read or fumble with a written checklist, which improves safety by reducing the workload. Furthermore, the computerized checklist system provides an accurate and consistent presentation of checklist items in sequence without the possibility of inadvertently omitting an item in the sequence.

It should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims.

What is claimed is:

1. In a computerized checklist system comprising a digital processor, storage means connected to the digital processor for storing alphanumeric checklist data including a sequence of checklist items, output means connected to the digital processor for selectively outputting checklist items, program control means for controlling the digital processor to effect presentation, by the output means, of the checklist items, and switch means for enabling an operator of the checklist system to enter one of a plurality of signals indicating that the operator has taken one of a plurality of predetermined actions in response to each checklist item outputted by the output means, the improvement comprising:

first control means, responsive to processing of the checklist items during a work session, for storing a session log, the session log including data identifying each checklist item outputted during the work session, the signal entered by the operator in response to each checklist item, and a time when such signal was entered by the operator;

second control means, responsive to completion of the work session, for deriving a verification code from the session log data, the verification code being uniquely associated with the session log data for the work session; and third control means for generating a printout of the session log in a predetermined format along with the verification code to facilitate subsequent verification of the session log data, the predetermined format including a checklist item field identifying checklist items outputted during the work session, an action field identifying, for at least one checklist item, the signal entered by the operator, and a time field identifying the time when such signal was entered by the operator.

2. The computerized checklist system as described in claim 1 wherein the predetermined format includes each checklist item in the order that such checklists items were outputted.

3. The computerized checklist system as described in claim 2 wherein the predetermined format further includes a title of a procedure defined by the checklist items, and indications when the procedure was initiated and completed.

4. The computerized checklist system as described in claim 1 wherein the data identifying the time is a real-time indication.

5. A computerized checklist system, comprising:
a checklist unit adapted to be held in an operator's hand, the checklist unit comprising:
a digital processor;
transmitting/receiving means controlled by the digital processor;
storage means connected to the digital processor for storing alphanumeric checklist data including a sequence of checklist items;
output means connected to the digital processor for selectively outputting checklist items;
program control means for controlling the digital processor to effect presentation, by the output means, of the checklist items; and
switch means for enabling an operator of the checklist unit to enter one of a plurality of signals indicating that the operator has taken one of a plurality of predetermined actions in response to each checklist item outputted by the output means;
means, responsive to processing of the checklist items during a work session, for storing a session log, the session log including data identifying each checklist item outputted during the work session, the signal entered by the operator in response to each checklist item, and a time when such signal was entered by the operator; and
a cradle for supporting the checklist unit, the cradle comprising:
a digital processor;
transmitting/receiving means controlled by the digital processor of the cradle;
program control means for controlling the digital processor of the cradle and including means responsive to placement of the checklist unit in the cradle for causing the session log data to be downloaded to the transmitting/receiving means of the cradle from the transmitting/receiving means of the checklist unit wherein the program control means of the cradle includes means for deriving a verification code from the session log data; and
a printer for receiving the downloaded session log data and generating a printout of the session log in a predetermined format, the verification code being included with the printout to facilitate subsequent verification of the session log data.

6. The computerized checklist system as described in claim 5 wherein the switch means of the checklist unit includes a GO button to enable the operator to enter an action complete signal indicating that a checklist item is completed.

7. The computerized checklist system as described in claim 5 wherein the switch means of the checklist unit includes first and second GO buttons, each of the GO buttons enabling an operator to enter an action complete signal indicating that a checklist item is completed.

8. The computerized checklist system as described in claim 7 wherein the checklist unit includes a housing having a front and a side, the first GO button located on the side of the housing and the second GO button located on the front of the housing.

9. The computerized checklist system as described in claim 5 wherein the switch means of the checklist unit includes a SKIP button to enable the operator to enter a skip signal indicating that the operator desires to delay completion of a response to a challenge.

10. The computerized checklist system as described in claim 5 wherein the switch means of the checklist unit includes an EXIT button to enable the operator to enter an exit signal indicating that the operator desires to exit a predetermined portion of a checklist being processed.

11. The computerized checklist system as described in claim 5 wherein the switch means of the checklist unit includes an N/A button to enable the operator to enter a not applicable signal indicating that a checklist item is not applicable to a procedure and need not be repeated.

12. The computerized checklist system as described in claim 5 wherein the switch means of the checklist unit includes a GET button to enable the operator to enter a get signal to retrieve another procedure for processing.

13. The computerized checklist system as described in claim 5 wherein the switch means of the checklist unit includes a HELP button to enable the operator to enter a help signal requesting output of predetermined information about a current checklist item or instructions for using the checklist unit.

14. The computerized checklist system as described in claim 5 wherein each of the transmitting/receiving means is a digital optical link.

* * * * *